United States Patent
Irudayaraj et al.

(10) Patent No.: US 12,031,983 B2
(45) Date of Patent: Jul. 9, 2024

(54) METHOD FOR LATERAL FLOW IMMUNOASSAY

(71) Applicant: Purdue Research Foundation, West Lafayette, IN (US)

(72) Inventors: Joseph Irudayaraj, Champaign, IL (US); Wen Ren, Urbana, IL (US)

(73) Assignee: Purdue Research Foundation, West Lafayette, IN (US)

( * ) Notice: Subject to any disclaimer, the term of this patent is extended or adjusted under 35 U.S.C. 154(b) by 314 days.

(21) Appl. No.: 17/502,320

(22) Filed: Oct. 15, 2021

(65) Prior Publication Data

US 2022/0146522 A1 May 12, 2022

Related U.S. Application Data

(63) Continuation of application No. 16/563,990, filed on Sep. 9, 2019, now abandoned.

(60) Provisional application No. 62/744,934, filed on Oct. 12, 2018.

(51) Int. Cl.
| | |
|---|---|
| *G01N 33/543* | (2006.01) |
| *B01L 3/00* | (2006.01) |
| *G01N 33/52* | (2006.01) |
| *G01N 33/569* | (2006.01) |
| *G01N 33/58* | (2006.01) |

(52) U.S. Cl.
CPC ...... *G01N 33/54388* (2021.08); *B01L 3/5023* (2013.01); *G01N 33/521* (2013.01); *G01N 33/56916* (2013.01); *G01N 33/586* (2013.01); *G01N 33/587* (2013.01)

(58) Field of Classification Search
CPC .............................................. G01N 33/54388
See application file for complete search history.

(56) References Cited

U.S. PATENT DOCUMENTS 10,006,906 B2    6/2018    Abbas

OTHER PUBLICATIONS

Bui et al., Nano Lett., 2015; 15(9): 6239-6246 (Year: 2015).*
Koczula et al., Essays in Biochemistry, 2016; 60: 111-120 (Year: 2016).*
Bui, Minh-Phuong Ngoc, Single-digit pathogen and attomolar detection with the naked eye using liposome-amplified plasmonic immunoassay. Nano Lett. 2015, 15(9), 6239-6246.
Chapman Robert, Multivalent Nanoparticle Networks Enable Point-of-Care Detection of Human Phospholipase-A2 in Serum. ACS Nano, 2015, 9(3), 2565-2573.
Cordeiro Milton, Gold Nanoparticles for Diagnostics: Advances towards Points of Care. Diagnostics (Basel). 2016, 6(4): 43.
Gomes J., Stable Polymethacrylate Nanocapsules from Ultraviolet Light-Induced Template Radical Polymerization of Unilamellar Liposomes. Langmuir 2006, 22, 7755-7759.
Virgen-Ortiz et al., J. Mater. Chem. B., 2017; 5: 7461-7490 (Year: 2017).

* cited by examiner

*Primary Examiner* — Brian Gangle
*Assistant Examiner* — Lakia J Jackson-Tongue
(74) *Attorney, Agent, or Firm* — Purdue Research Foundation

(57) ABSTRACT

The present disclosure relates to a novel method for lateral flow immunoassay (LFIA) by utilizing plasmonic enhancement strategy. More specifically, the present disclosure provides a plasmonic enhanced lateral flow sensor (pLFS) concept by introducing a liposome-based amplification of the colorimetric signals on the lateral flow platform for ultrasensitive detection of pathogens.

8 Claims, 7 Drawing Sheets

METHOD FOR LATERAL FLOW IMMUNOASSAY

CROSS-REFERENCE TO RELATED APPLICATION

This application is a continuation of U.S. application Ser. No. 16/563,990, filed Sep. 9, 2019, which claims the benefit of U.S. Provisional Application Ser. No. 62/744,934, filed Oct. 12, 2018, the contents of which are incorporated herein entirely.

GOVERNMENT RIGHTS

This invention was made with government support under contract number 59-8072-6-001 awarded by the U.S. Department of Agriculture. The government has certain rights in the invention.

TECHNICAL FIELD

The present disclosure relates to a novel method for lateral flow immunoassay (LFIA) by utilizing plasmonic enhancement strategy, and compositions used for the method.

BACKGROUND

This section introduces aspects that may help facilitate a better understanding of the disclosure. Accordingly, these statements are to be read in this light and are not to be understood as admissions about what is or is not prior art.

Lateral flow immunoassay (LFIA) has held its place as a very practical analytical method for the detection and evaluation of various targets including nucleic acids, protein, and whole organisms such as virus and bacteria because of its simplicity and onsite usability. LFIA has been used in food safety and public health screening including clinical diagnosis for point-of-care testing and in-situ monitoring. LFIA systems based on fluorescence or other spectral analysis require instrumentation for signal readout, while colorimetric signals are easier to use because of the direct inspection of results with naked eyes. Signals from colorimetry are usually weak hence sensitive detection is not possible. To improve the sensitivity of colorimetric LFIA several prior work exists with polymer nanoparticles or latex beads loaded with color inducing chemicals while metal nanoparticles are still commonly used as substrates for LFIA probes. Metal nanoparticles, due to its plasmonic feature, usually has large extinction coefficient, and thus a small amount of nanoparticles could provide a visible color. Among metal nanoparticles, gold nanoparticles (GNPs) have been widely used in LFIA colorimetry because of its stability and biocompatibility. In spite of the large extinction coefficient detecting at low target levels with GNPs induced colorimetry is still a challenge since the color generated from the probes anchored at the detection zone is very weak. The limit of detection (LOD) possible for whole cell detection with conventional LFIA was around $10^5$-$10^6$ CFU/ml, which is not sufficient for effective food safety monitoring. Hence, enhancement of the colorimetric signal is critical for LFIA applications.

Enzyme based colorimetric signal amplification was suggested to provide higher enhancement. When enzymes are conjugated to the probes, the presence of targets was represented by the color generated from the enzyme-catalyzed reaction products. However, it should be noted that the enzyme catalyzed reaction could be influenced by the detection environment and the presence of non-targets in real samples contributing to nonspecific signals, while the stability of bioactive enzyme modified probes would limit the application. Thus, a non-reaction based enhancement strategy for colorimetric LFIA could further advance this technology.

Based on the concept of color change due to the aggregation of GNPs, Abbas et al proposed a liposome based plasmonic enzyme-linked immunosorbent assays (ELISA) method, where liposomes loaded with L-cysteine was used to label the target. See Bui, M.-P.N., Ahmed, S., Abbas, A., 2015. Single-digit pathogen and attomolar detection with the naked eye using liposome-amplified plasmonic immunoassay. Nano Lett. 15(9), 6239-6246. However, the method took place in liquid solutions and took 3-4 hours to provide the results.

Therefore, there is an unmet need for faster, reliable, and enhanced colorimetric signal method for LFIA in detection of analytes such as pathogens.

SUMMARY

The present disclosure relates to a novel method for lateral flow immunoassay (LFIA) by utilizing plasmonic enhancement strategy.

In one embodiment, the present disclosure provides a method of detecting one or more target analytes in a liquid sample, wherein the method comprises:
a) providing a lateral flow strip, wherein the lateral flow strip comprises a sample pad to receiving a liquid sample, a conjugate pad, and a sample capture area having pre-loaded antibodies that are capable of binding a target analyte;
b) preparing a liquid sample comprising a mixture of a target analyte, streptavidin, gold nanoparticles (GNPs) probes comprising biotinylated and antibody modified gold nanoparticles (GNPs), and an amine-containing chemical loaded liposomes;
c) loading said liquid sample solution to the sample pad of the lateral flow strip and let the liquid sample migrate along the lateral flow strip to let the target analyte bind with the pre-loaded antibody on the capture area; and
d) providing a detecting agent comprising gold nanoparticles and a hydrolytic agent and allowing the detecting agent to contact the lateral flow strip one or more times to generate a colorimetric signal that shows the existence of the target analyte, wherein the hydrolytic agent is capable of hydrolysis of said liposomes to release said amine-containing chemical.

In one embodiment, the present disclosure provides a liquid composition comprising a mixture of streptavidin, gold nanoparticles (GNPs) probes comprising biotinylated and antibody modified gold nanoparticles (GNPs), and an amine-containing chemical loaded liposomes.

DETAILED DESCRIPTION

Figure 1:
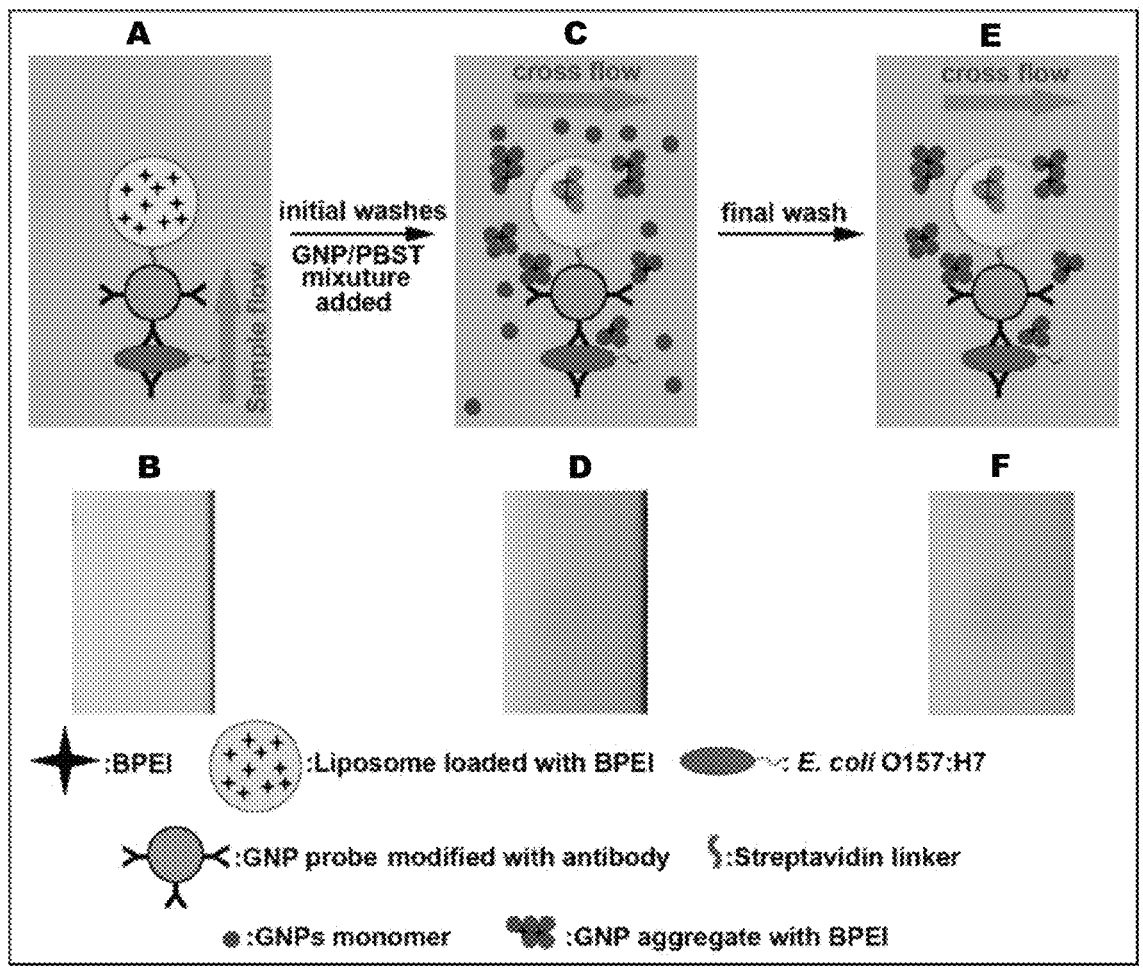
FIG. 1 shows the general concept of the plasmonic enhanced lateral flow immunoassay. (A) shows that the labeled E. coli O157:H7 is captured by antibodies immobilized on the LF strip to form a structure comprising of antibody on strip/captured target bacterium/labeled GNP probe/linked liposome loaded with BPEI. (B) shows that there was no visible color on the LF strip, suggesting that the limited number of GNP probes conjugated to the LF strip due to the low concentration of target bacteria will not generate any signal. (C) shows that PBST will rupture the liposomes and release BPEI. The released BPEI will cross-link with the added GNPs to initiate its aggregation. (D) shows that the obtained aggregates as shown in (C) were distributed in the detection zone where the liposomes were anchored, represented by the red spot. (E) shows the result after one more wash by GNP/PBST mixture. (F) shows the cleaner result after one more wash by GNP/PBST mixture.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "solution" refers to a homogeneous or substantially homogeneous mixture composed of two or more substances. In some aspects, the term "solution" may refer to a colloid mixture as far as the mixture is visually clear/transparent and is a homogeneous or substantially homogeneous mixture composed of two or more substances.

The present disclosure provides a plasmonic enhanced lateral flow sensor (pLFS) concept by introducing a liposome-based amplification of the colorimetric signals on the lateral flow platform for ultrasensitive detection of pathogens. In pLFS, liposomes loaded with chemicals were anchored at the detection zone in the presence of targets. The liposomes are ruptured to release the chemical to trigger the aggregation of GNPs. The resulting aggregates of GNPs were trapped in the framework of nitrocellulose membrane after washing to form red spots. In the absence of target no liposomes were present in the detection zone and no aggregation occurred, hence the added GNP monomers were washed away and did not give rise to any color on the LF strip. Thus, the colorimetric signal from the trapped aggregates of GNPs could determine the target captured. A branched polyethylenimine (BPEI) was loaded in the liposomes to facilitate the cross-linking and aggregation of GNPs due to the amino groups. Compared to the signals from conventional LFIA systems with GNPs themselves, a stronger colorimetric signals in pLFS originated from the trapped GNP aggregates, to result in better sensitivity. Since enzymes were not required, the deviation of enzyme activity and non-specific interaction in the pLFS can be avoided.

To demonstrate the detection performance of the pLFS concept proposed in the present disclosure, E. coli O157:H7 was chosen as the target. It is known as the Shiga toxin-producing pathogen could induce various diseases to result in up to 40% mortality and thus is a serious threat to food safety and public health. The proposed pLFS could recognize as low as 100 CFU/ml of E. coli O157:H7 within 45 min, which is over 1000 times more sensitive than the LOD possible by conventional LFIA ($10^5$-$10^6$). The detection time by pLFS was much shorter than ELISA which requires 3-4 hrs. The capability of pLFS was also demonstrated in liquid food such as cranberry juice, and a LOD of 600 CFU/ml of E. coli O157:H7 was possible. The developed plasmonic enhancement strategy is unique and versatile for rapid onsite detection.

In one embodiment, the present disclosure provides a method of detecting one or more target analytes in a liquid sample, wherein the method comprises:
a) providing a lateral flow strip, wherein the lateral flow strip comprises a sample pad to receiving a liquid sample, a conjugate pad, a sample capture area having pre-loaded antibodies that are capable of binding a target analyte;
b) preparing a liquid sample comprising a mixture of a target analyte, streptavidin, gold nanoparticles (GNPs) probes comprising biotinylated and antibody modified gold nanoparticles (GNPs), and an amine-containing chemical loaded liposomes;
c) loading said liquid sample solution to the sample pad of the lateral flow strip and let the liquid sample migrate along the lateral flow strip to let the target analyte bind with the pre-loaded antibody on the capture area; and
d) providing a detecting agent comprising gold nanoparticles and a hydrolytic agent and allowing the detecting agent to contact the lateral flow strip one or more times to generate a colorimetric signal that shows the existence of the target analyte, wherein the hydrolytic agent is capable of hydrolysis of said liposomes to release said amine-containing chemical.

In one embodiment, the target analyte comprises a pathogen. In one aspect, the pathogen is food a pathogen. In one aspect, the pathogen is E. coli O157:H7, Salmonella sp., Listeria sp., or any combination thereof.

In one embodiment, the amine-containing chemical is branched polyethylenimine, cysteine, salt or derivative therefore, or any combination thereof. In one aspect, the amine-containing chemical is branched polyethylenimine with molecular weight range of about 300-10000, 500-7500, 750-5000, 1000-2500 daltons, or any combination thereof.

In one embodiment, the existence of a target analyte can be observed by naked human eyes through colored line and/or spot corresponding to the availability of the target analyte.

In one embodiment, the target analyte can be identified no more than about one hour period. In one aspect, the target analyte can be identified within about 45 minutes.

In one embodiment, there is no enzyme used in the method.

In one embodiment, the hydrolytic agent may be but is not limited to polyoxyethylene (20) sorbitan monolaurate (Tween-20). The hydrolytic agent is used to break liposomes.

In one embodiment, the present disclosure provides a liquid composition comprising a mixture of streptavidin, gold nanoparticles (GNPs) probes comprising biotinylated and antibody modified gold nanoparticles (GNPs), and an amine-containing chemical loaded liposomes, wherein the composition is used to bind to a target analyte.

In one embodiment, the present disclosure provides a liquid composition comprising a mixture of a target analyte, streptavidin, gold nanoparticles (GNPs) probes comprising biotinylated and antibody modified gold nanoparticles (GNPs), and an amine-containing chemical loaded liposomes.

In one embodiment, the present disclosure provides a complex, wherein the complex comprises a target analyte moiety, a streptavidin moiety, a gold nanoparticles (GNPs) probe moiety comprising biotinylated and antibody modified gold nanoparticle (GNPs), and an amine-containing chemical loaded liposome moiety, wherein the target analyte moiety is connected to the gold nanoparticles (GNPs) probe moiety through an antibody moiety, and the gold nanoparticles (GNPs) probe moiety is connected to the amine-containing chemical loaded liposome moiety through the streptavidin moiety.

In one embodiment, the present disclosure provides a complex, wherein the complex comprises a target analyte moiety, a streptavidin moiety, a gold nanoparticles (GNPs) probe moiety comprising biotinylated and antibody modified gold nanoparticle (GNPs), and an amine-containing chemical loaded liposome moiety, wherein the target analyte moiety is connected to the gold nanoparticles (GNPs) probe moiety through a first antibody moiety on the gold nanoparticles, the gold nanoparticles (GNPs) probe moiety is further connected to the amine-containing chemical loaded liposome moiety through the streptavidin moiety, wherein the target analyte moiety is further connected with a second antibody that is pre-anchored on a lateral flow strip to ensure that the whole complex is anchored on the lateral flow strip.

Experimental Section

Materials $HAuCl_4 \cdot 3H_2O$, sodium citrate dihydrate, $Na_2CO_3$, BPEI (Mn=~1800) and cholesterol were purchased from Sigma-Aldrich (St. Louis, MO). L-α-phosphotidylcholine (PC) and phosphoethanolamine-conjugated biotin (DSPE-PEG2000-biotin) were obtained from Avanti Polar Lipids (Alabaster, AL). Sulfo-NHS-LC-biotin was purchased from Thermal Scientific (Rockford, IL). Polyclonal antibody against *E. coli* O157:H7 (01-95-90) and heat-treated *E. coli* O157:H7 for positive control were acquired from KPL (Gaithersburg, MD). All chemicals were used as received. All glasswares were cleansed with fresh aqua regia and rinsed with DI water.

Preparation of GNPs and GNP Probes

GNPs used for pLFS were synthesized based on the reported method. See Frens, G., 1973. Controlled nucleation for regulation of particle-size in monodisperse gold suspensions. Nature-Phys. Sci. 241(105), 20-22. Briefly, 1 ml of 1% $HAuCl_4 \cdot 3H_2O$ was added to 100 ml of boiling DI water. To the obtained 18 nm GNPs, under strong stirring, 1 ml of 1% sodium citrated was added and the solution was kept at boiling for an additional 15 min. For 40 nm GNPs, 0.5 ml of 1% sodium citrate was added. The obtained GNPs were cooled down to room temperature and kept at 4° C. for subsequent experiments. The size and concentration was calculated with the method reported by Haiss et al. based on the UV-vis spectra collected with a Genesystm 10S UV-vis Spectrophotometer. See Haiss, W., Thanh, N. T., Aveyard, J., Fernig, D. G., 2007. Determination of size and concentration of gold nanoparticles from UV-Vis spectra. Anal. Chem. 79(11), 4215-4221.

GNP probes were fabricated based on previously reported method with modification. See Cho, I.-H., Irudayaraj, J., Lateral-flow enzyme immunoconcentration for rapid detection of Listeria monocytogenes. Anal. Bioanal. Chem. 2013, 405(10), 3313-3319; Ren, W., Cho, I.-H., Zhou, Z., Irudayaraj, J., 2016. Ultrasensitive detection of microbial cells using magnetic focus enhanced lateral flow sensors. Chem. Commun. 52(27), 4930-4933; and Ren, W., Liu, W., Irudayaraj, J., 2017. A net fishing enrichment strategy for colorimetric detection of *E. coli* O157: H7. Sens Actuator B-Chem 247, 923-929. Briefly, 500 µl of 40 nm GNPs were added with 50 µl of 10 mM PB buffer, followed by the addition of 1 µl of 0.5 M $Na_2CO_3$. After mixing well, 5 µl of 1 mg/ml polyclonal antibody against *E. coli* O157:H7 was injected. The obtained solution was shaken for 4 hours at room temperature. Then 55 µl of 5% casein in 10 mM PB buffer was added and shaken for 1 hour to block the unreacted surface. The obtained GNPs was centrifuged at 8000 rpm for 10 min and washed with 10 mM PB buffer two times. After redispersing in 500 µl of 10 mM PB buffer, the antibody modified GNPs were biotinylated by the addition of 10 µg sulfo-NHS-LC-biotin and the solution was shaken at room temperature for 1 hour. The resulting GNP probes were washed with 10 mM PBS buffer two times and redispersed in 500 µl of 10 mM PBS.

Synthesis of BPEI-loaded liposome

The synthesis of liposomes loaded with BPEI was performed based on published methods with slight modification. See Bui, M.-P.N., Ahmed, S., Abbas, A., 2015. Single-digit pathogen and attomolar detection with the naked eye using liposome-amplified plasmonic immunoassay. Nano Lett. 15(9), 6239-6246. In a reserve-phase evaporation process, 140 µl of 5 mg/ml PC in chloroform was added with 20 µl of 5 mg/ml cholesterol in chloroform and 40 µl of 5 mg/ml DSPE-PEG2000-biotin in chloroform in a glass vial. After rotation for the formation of a uniform layer of the solution, the glass vial was vacuumed overnight to evaporate the chloroform. To the glass vial, 1 ml of 100 m/ml BPEI was added and the solution was vortexed for 2 min to result in the formation of cloud-like multilamellar liposomes. The prepared liposomes were purified by dialysis with a dialysis membrane (MWCO 14 kDa, Spectrum, Inc., Rancho Dominguez, CA) and the size of the obtained liposome was determined to be 172.6±6.5 nm with a dynamic light scattering particle size analyzer (Malvern Zetasizer ZS90). The concentration of liposome was estimated to be around $1.73 \times 10^{11}$ liposome/ml based on the procedure described by Abbas et al. See Bui, M.-P. N., Ahmed, S., Abbas, A., 2015. Single-digit pathogen and attomolar detection with the naked eye using liposome-amplified plasmonic immunoassay. Nano Lett. 15(9), 6239-6246.

Plasmonic enhanced lateral flow sensor development

Lateral flow strips were assembled on a plastic backboard, on which 2.5 cm length of nitrocellulose membrane was fixed at a position of 1.3 cm from one end of the strip. An absorbent pad 1.5 cm in length was fixed at the end of the strip, while at the other end of the nitrocellulose membrane, a 1.1 cm of conjugate pad and 1.7 cm of sample pad was assembled on the plastic backboard. Each part had a 0.2 cm overlap area to ensure continuity in sample flow. The width of the strip was set at 0.5 cm. On the prepared LF strip, 0.9 µl of 0.33 mg/ml of polyclonal antibody against E. coli O157:H7 was dropped on the nitrocellulose membrane and the strip was dried at 37° C. for 1 hour.

To detect bacteria, 100 µl of sample solution containing serial concentration of E. coli O157:H7 was added with 5 µl of GNP probes and 0.5 µl of 1 mg/ml streptavidin. Then the sample was incubated at room temperature for 10 min, followed by the addition of 5 µl of BPEI-loaded liposomes. After 5 min of incubation, the sample solution was loaded on the sample pad of the lateral flow strip for 10 min of sample flow. A conjugate pad and an absorbent pad at 1.1 cm×1.3 cm were fixed at both sides of the strip respectively and 60 µl of DI water was added to the conjugate pad to wash the detection zone twice at 5 min interval. Then 60 µl of GNPs in PBST (1:2 ratio, PBST: 0.5% tween-20 in 10 mM PBS) was added for colorimetric signal generation. After 5 min, 60 µl of DI water was applied for one more wash and the results were recorded with a camera.

Cranberry juice was obtained from a local grocery store and its pH was adjusted with 1M NaOH. To reduce the influence from thickening agents the juice was diluted with 10 mM PBS at 1:1 ratio. Known concentration of E. coli O157:H7 was purposefully inoculated into the juice sample and the resulting solution was used as a food sample in the pLFS.

All experiments were replicated 3 times. To quantify the colorimetric signals, images of the strips were recorded after detection. The brightness and contrast of the images was adjusted and converted to monochrome format. Then ImageJ was used to measure the gray scale value of the dots from the GNP aggregates and the blank area around the dots. The difference between the gray scale value from dots and corresponding blank area was used for quantification.

Results

The plasmonic enhancement concept implemented in a lateral flow devise utilizing liposomes encompass the advantages of plasmonic ELISA while retaining the merits of a lateral flow devise. The plasmonic enhancement strategy of pLFS is illustrated in FIG. 1. The target E. coli O157:H7 is first labeled with GNP probes which comprise of gold nanoparticles modified with antibody and biotinylated. The BPEI-loaded liposome particles were then linked to GNP probes through streptavidin-biotin linkage. In the sample flow along the strip, as shown in FIG. 1a, the labeled E. coli O157:H7 is captured by antibodies immobilized on the LF strip to form a structure comprising of antibody on strip/captured target bacterium/labeled GNP probe/linked liposome loaded with BPEI. It can be seen in FIG. 1b that there was no visible color on the LF strip, suggesting that the limited number of GNP probes conjugated to the LF strip due to the low concentration of target bacteria will not generate any signal. After two initial washes via cross flow, the GNPs/PBST mixture was added on the strip as shown in FIG. 1c. PBST will rupture the liposomes and release the BPEI. The released BPEI will cross-link with the added GNPs to initiate its aggregation. The obtained aggregates were distributed in the detection zone where the liposomes were anchored, represented by the red spot in FIG. 1d. The color change from red to blue due to aggregation of GNPs was also not observed on the LF strip, which may be attributed to the limited space in the nitrocellulose membrane where the amount of added GNPs was not sufficient to form larger aggregates to cause the color change. At the final washing step, GNP monomers were removed along with the washing solution. In contrast, aggregates of GNPs due to the presence of BPEI were retained in the detection zone since the aggregates were larger in size compared to the GNP monomers and could not be removed from the LF strip with the washing solution. It should be noted that the GNPs at the sites away from the red dots did not aggregate because the amount of BPEI released was not sufficient to induce aggregation and thus were removed in the last wash step. FIG. 1f shows that the red spot remained in the detection zone while the rest of the region on the strip was cleaner than that shown in FIG. 1d, providing evidence that after the final wash the aggregates of GNPs linked by BPEI were retained in the nitrocellulose membrane and the GNP monomers were removed. Images shown as FIG. 1b, 1d, 1f reveal the detection mechanism of the developed pLFS: without target bacteria, no liposome was retained in the detection zone after initial washing steps, thus GNPs present in the monomer form were washed away in the final wash; in the presence of target bacteria the BPEI-loaded liposome would be anchored in the detection zone through the labeled probe, where the released BPEI could cross-link the added GNPs to form aggregates which remained in nitrocellulose membrane after washing to result in visible red dots. An increase in the concentration of target bacteria would link more liposomes and the corresponding increase in BPEI released could contribute to the formation of more aggregates to result in higher intensity of red dots in the detection zone.

Figure 2:
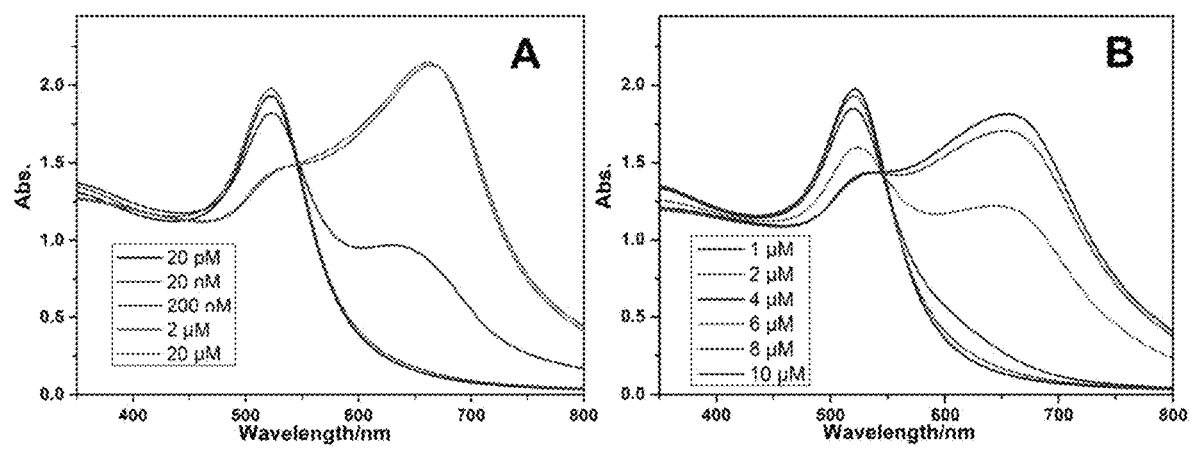
FIG. 2 shows UV-spectra of 18 nm GNPs with serial concentration of BPEI (A) and L-cysteine (B).

To demonstrate the aggregation behavior of GNPs with BPEI, UV-vis spectra of GNPs were recorded with BPEI or L-cysteine at serial concentration in PBST and the spectra were shown in FIG. 2. It can be seen that a significant aggregation of 18 nm GNPs occurred at 200 nM BPEI concentration while to observe the aggregation of GNPs~4 µM or more of L-cysteine was required, suggesting improved sensitivity with BPEI. With 200 nM BPEI a strong absorption at 600 nm or greater indicated the cross-linking of GNPs with BPEI linkers contributing to the color change. The improved ability of BPEI to trigger the aggregation of GNPs could be attributed to the multiple amino groups in a branched molecular structure and larger molecular size of BPEI. On the LF strips, since there was very limited solution in the nitrocellulose membrane, few BPEI molecules released from the liposome conjugated to the target bacteria could induce an observable cross-linking of GNPs.

Figure 3:
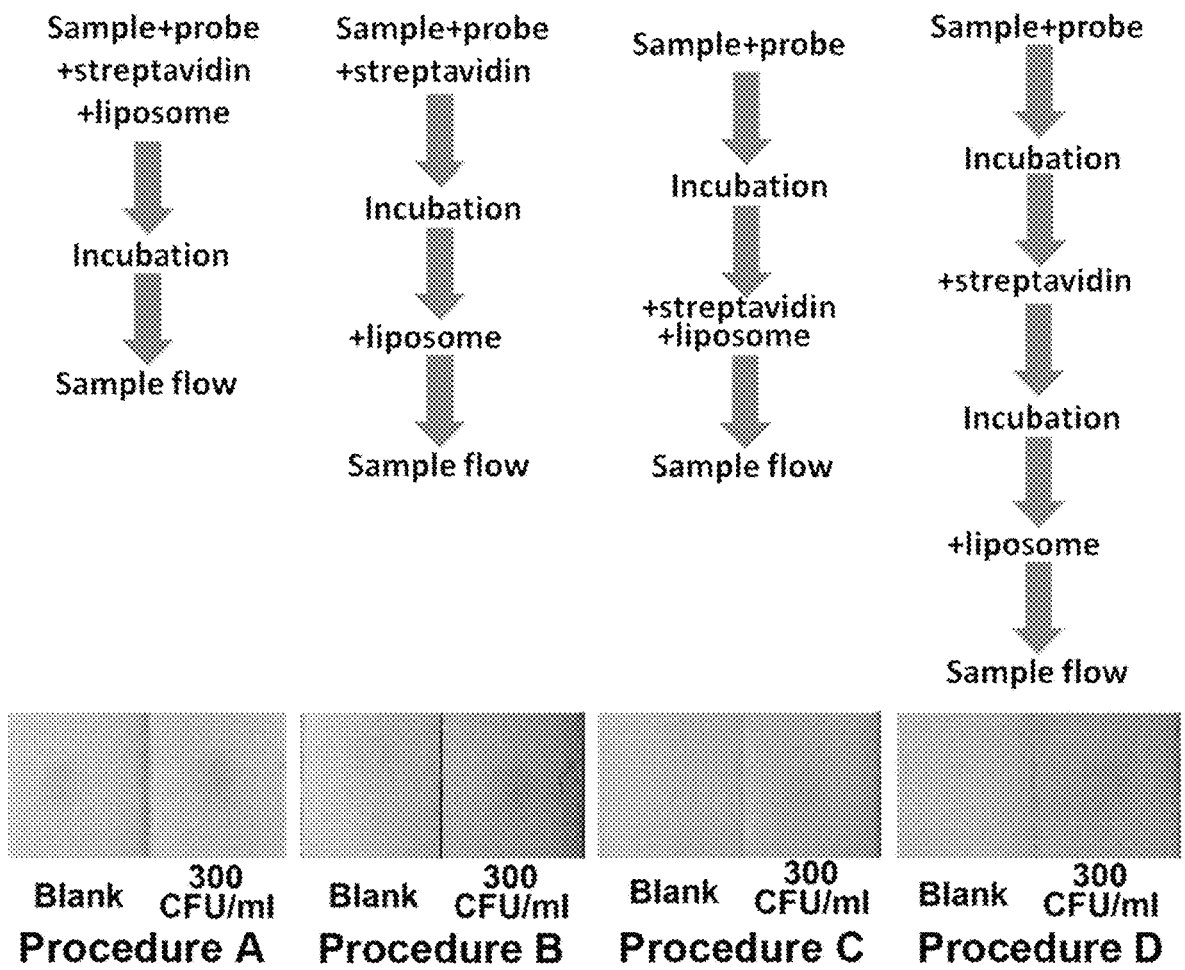
FIG. 3 shows schematic of sample preparation steps and representative results (photos) in pLFS experiments from blank samples for E. coli O157:H7 concentration of 300 CFU/ml.

In ELISA, the capture of target, the labeling of probes and liposome as well as the color change due to GNP aggregation were performed in separate steps with a washing step interval. In contract, in LFIA the same process would have to be performed on the LF strip sequentially. Thus, in the pLFS detection the timing of the addition of probes, streptavidin linker, liposomes and GNPs/PBST mixture is very important for appropriate generation of colorimetric signal. Different detection procedures were investigated to achieve optimal performance. In FIG. 3, various detection procedures were illustrated along with the corresponding results. It was noted that in Procedure A when the probes, streptavidin and liposomes are directly mixed with the sample, there was an observable red dot with the blank, which could be attributed to the cross-linking of the probe-liposome structures trapped in the detection zone giving rise to the signal in the following colorimetric generation process. The resulting signal from the blank could be recognized as false positives to influence the reliability of the detection method. Procedures B, C, and D exhibited a clear strip with blank samples, hence false positive was not a concern. These clear strips from blank samples also suggested that the possible cross-linked probes would not induce false positives without liposome. In our evaluation, Procedure C gave the weakest positive signal, suggesting the least sensitivity. Compared with Procedure B, in Procedure C there were more unreacted streptavidin linkers when liposomes were added to induce more liposome network structures. But no obvious spot was noted in Procedure C, suggesting that the cross-linked liposome network structures would not result in false positives which could be attributed to the low concentration of liposomes ($1.73\times10^{11}$ liposomes/ml). The weaker signal in Procedure C with E. coli O157:H7 compared to that in Procedure B implied that the formed cross-linked liposome network structures would reduce the number of liposomes linked to the probes labeling the captured E. coli O157:H7 in the detection zone resulting in low sensitivity. The strongest signal was obtained from Procedure D, however the most complex operation and longer process limited the simplicity and practicality of pLFS, further the intense color in the region around the dot in the detection zone made it hard to recognize the spot from the rest of the area. The difference in results obtained above in the listed procedures indicated that the cross-linked probe-liposome structures should be the main reason for false positives in pLFS. Upon evaluation, Procedure B was chosen as the optimized protocol for the pLFS in the following experiments.

Figure 4:
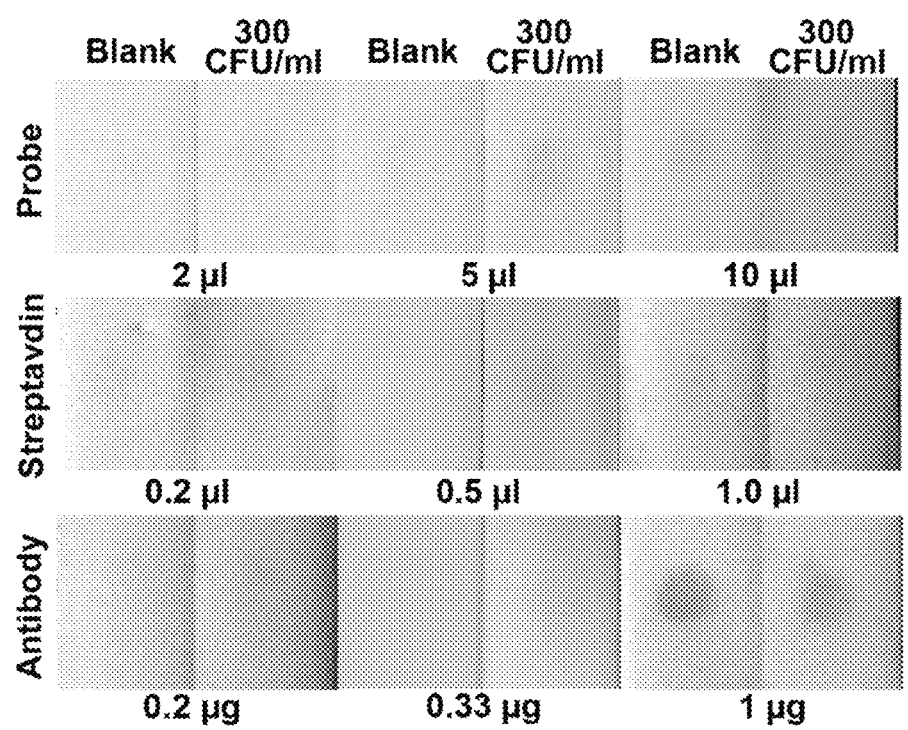
FIG. 4 shows photos of LF strip with blank sample (control) and 300 CFU/ml of E. coli O157:H7 from pLFS performed under different experimental conditions.
Figure 5:
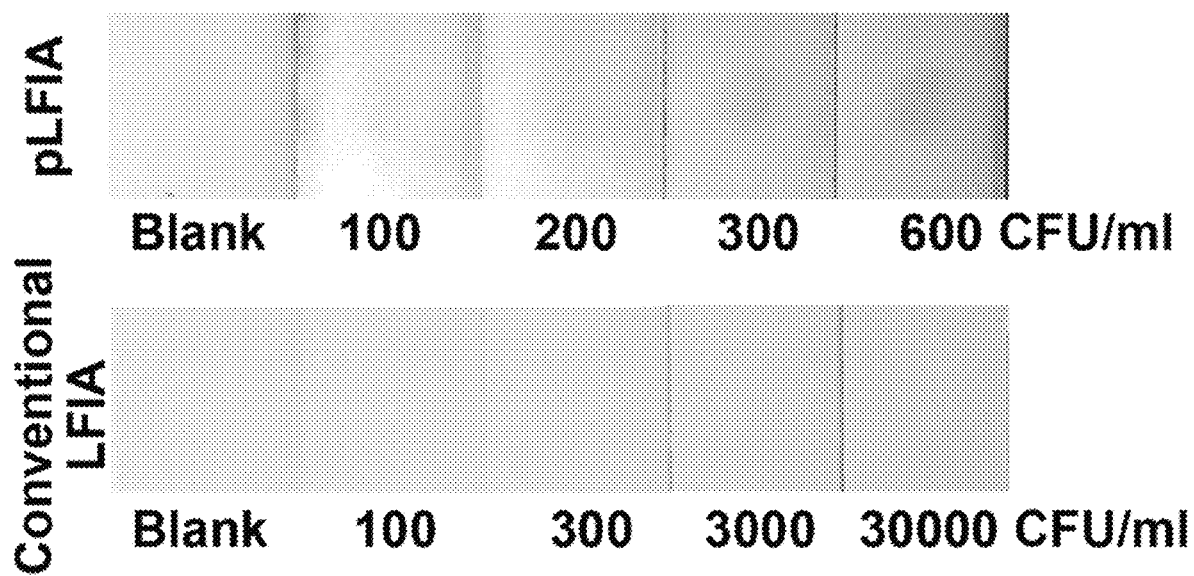
FIG. 5 shows comparison between pLFS and conventional LFIA response to serial concentration of E. coli O157:H7.

In the pLFS procedure, detection results could be affected by the amount of probes and streptavidin linker incubated with target bacteria in the solution. Meanwhile the antibody immobilized on the LF strip could also influence detection sensitivity. To investigate these factors for the pLFS methodology, serial optimizations were performed. FIG. 4 shows images of the LF strips obtained from pLFS performed under different conditions. It can be seen that when the added GNP probes increased to 10 µl, the obtained signal from a 300 CFU/ml of E. coli O157:H7 sample became more intense while a blank signal was noticeable. The reason for an increase in signal strength at 300 CFU/ml of E. coli O157:H7 is due to the increased amount of probes on the target bacteria; however, at higher concentrations, the probes may increase the amount of cross-linked probe-liposome structures trapped in the detection zone to give rise to false positives. It should be noted that the increase in streptavidin did not significantly improve the signals from bacteria compared with blank samples. The attributed reasons are: higher concentration of streptavidin could increase the possibility to cross-link probes and liposomes; however, since the streptavidin (1.8 uM) was present at a much higher concentration than the probes (0.17 nM) and liposomes ($1.73\times10^{11}$ liposomes/ml), the change in the concentration of streptavidin would not be a key factor to the formation of cross-linked probe-liposome structures. Based on the results in optimization of detection procedure and conditions, we hypothesized that the cross-linked probe-liposome structures should be the main reason for false positive signals. The excess streptavidin did not contribute to any significant improvement in the signal from the sample with 300 CFU/ml of E. coli O157:H7. The amount of antibody conjugated on the LF strip could affect the results of pLFS. It can be seen that with 1 µg of antibody an intense spot was observed with blank samples though the signals from 300 CFU/ml of E. coli O157:H7 was better than the others, indicating that the density of antibodies in the detection zone should be a key factor in the concentration of trapped probe-liposome cross-linked structures which could result in false positives with blank samples. Meanwhile higher concentration of antibodies immobilized on the strip was found to increase the signal at 300 CFU/ml of E. coli O157:H7. However, when the amount of antibody immobilized on the LF strip was reduced to 0.2 µg, no signal was observed with the blank sample or 300 CFU/ml of E. coli O157:H7, which could be attributed to a lower amount of labeled target bacteria captured at the detection zone. According to the results shown in FIG. 4, the cross-linked probe-liposome structures should be the main reason for false positives, while the amount of probes and antibodies immobilized on the LF strip could affect the detection results more than that of the added streptavidin and liposome. To demonstrate plasmonic enhancement of the proposed pLFS, serial concentrations of E. coli O157:H7 from 100 to 600 CFU/ml were evaluated based on the optimized protocol. Images of the final results from pLFS was illustrated in FIG. 5. To further illustrate the detection performance of pLFS, a comparison was made with conventional LFIA to detect E. coli O157:H7 under same condition. It can be seen that with the developed pLFS as low as 100 CFU/ml of bacteria could be recognized with naked eye. However, with conventional LFIA, no visible signal could be observed even at 30000 CFU/ml of bacteria. The comparison demonstrated a dramatically improved LOD from pLFS than the conventional LFIA performed under the same conditions. In contrast, the sensitivity of the reported LFIA with silver enhanced LFIA was increased by only 10 times, See Wiederoder, M., Smith, S., Madzivhandila, P., Mager, D., Moodley, K., DeVoe, D., Land, K., 2017. Novel functionalities of hybrid paper-polymer centrifugal devices for assay performance enhancement. Biomicrofluidics 11(5), 054101, while the pLFS was comparable to the enzyme amplified LFIA which was shown to detect as low as 100 CFU/ml of bacteria. See Cho, I.-H., Irudayaraj, J., 2013b. Lateral-flow enzyme immunoconcentration for rapid detection of Listeria monocytogenes. Anal. Bioanal. Chem. 405(10), 3313-3319. A key advantage of pLFS is that the enhancement strategy does not depend on enzymes for color generation and hence has immense practical appeal. It should also be noted from the images, that an increased intensity of red color from pLFS is proportional to the concentration of E. coli O157:H7, suggesting its potential in quantitation.

Figure 6:
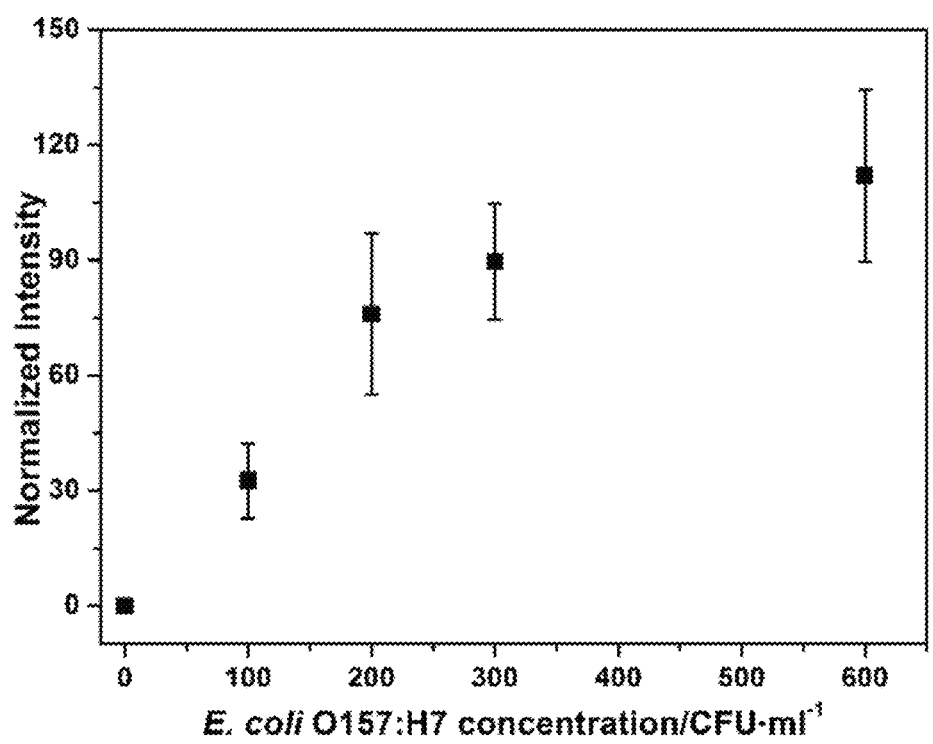
FIG. 6 shows Quantitative response of the colorimetric signal from pLFS when exposed to E. coli O157:H7 at different concentration [mean±SD, n=3].

To quantify the response of pLFS, the results based on the intensity of the spots from the samples at a serial concentration of E. coli O157:H7 is plotted (FIG. 6). The normalized intensity of the red spots was calculated based on the gray scale value of the spots in the images relative to the results from blank samples as the baseline. It can be seen that the normalized intensity of the dots increased with the concentration of target bacteria. It was also noted that the percent increase in color intensity for concentration range from 300 CFU/ml to 600 CFU/ml was not as much as that from 0 to 300 CFU/ml, which could be attributed to the number of GNP aggregate formation limited by the amount of GNP monomers possibly confined by the pores of the nitrocellulose membrane in the LF strip.

Figure 7:
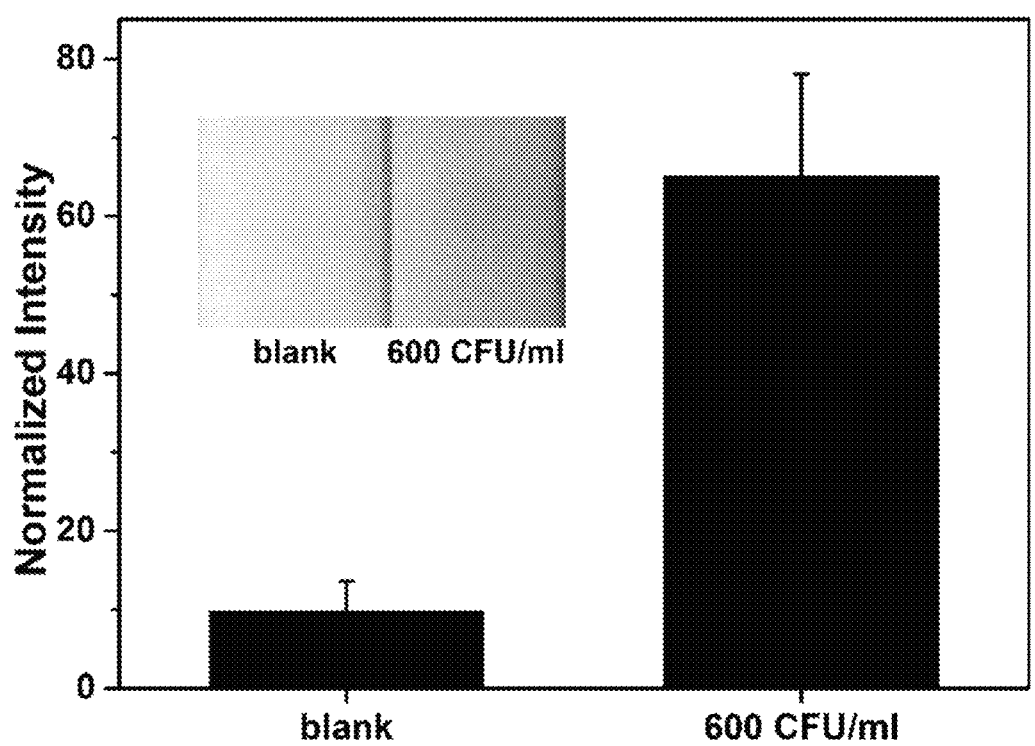
FIG. 7 shows the quantitative response from blank and 600 CFU/ml of E. coli O157:H7 in 1:1 ratio diluted cranberry juice [mean±SD, n=3]. Inset is representative image from detection results in cranberry juice.

To investigate the detection performance of the proposed pLFS in food samples, cranberry juice obtained from a local market was inoculated with E. coli O157:H7 and used in experiments. Since the pH of the packaged juice was around 4 which could potentially influence the antibody capture and probe label, the pH was adjusted to 7 with 1 M NaOH. To reduce the influence from thickening agents in the juice, the juice was diluted with 10 mM PBS in 1:1 ratio. The quantified detection results from pLFS were shown in FIG. 7 and the inset in FIG. 7 shows the image of the strip after experimentation. It can be seen that compared with the results from the bacteria in PBS, the blank juice gave a slight background signal as expected due to interference from the food matrix. Likewise, the quantified signal from 600 CFU/ml in juice (FIG. 7) was weaker than that in PBS (FIG. 6). Although in the inset in FIG. 7, the color signal from 600 CFU/ml of E. coli O157:H7 in juice was weaker than the one from PBS (FIG. 5) and a red dot can still be recognized, indicating the potential of the proposed pLFS in food sample monitoring.

The plasmonic enhancement concept was developed and implemented in an LFIA device utilizing BPEI-loaded liposomes to trigger the aggregation on GNPs for signal generation. The detection procedure complies with the simplicity of the conventional LFIA systems in the market. With the plasmonic enhancement strategy, the detection sensitivity of the pLFS was greatly enhanced rather than that based on the color of probes themselves. The detection procedure and conditions were investigated to achieve optimized performance to detect as low as 100 CFU/ml of E. coli O157:H7, which is 1000 folds better than the conventional LFIA platforms and comparable to the enzyme amplified LFIA. Meanwhile with pLFS, 600 CFU/ml of E. coli O157:H7 can be recognized with naked eyes in juice samples. The pLFS concept developed does not require enzymes for color generation or enhancement and thus eliminates issues related to enzyme stability and bioactivity inherent to enzyme-based colorimetric reaction. Results indicate that the proposed pLFS exhibits a strong potential for detecting various bacteria targets. Meanwhile by loading different chemicals in the liposome, the pLFS platform could provide the flexibility for signal enhancement to detect multiple targets.

Those skilled in the art will recognize that numerous modifications can be made to the specific implementations described above. The implementations should not be limited to the particular limitations described. Other implementations may be possible.

We claim:

1. A method of detecting one or more target analytes in a liquid sample, wherein the method comprises:
    a) providing a lateral flow strip, wherein the lateral flow strip comprises a sample pad to receiving a liquid sample, a conjugate pad, a sample capture area having pre-loaded antibodies that are capable of binding a target analyte;
    b) preparing a liquid sample comprising a complex that comprises a target analyte, streptavidin, gold nanoparticles (GNPs) probes comprising biotinylated and antibody modified gold nanoparticles (GNPs), and an amine-containing chemical loaded liposomes, wherein said streptavidin serves as a linker between said gold nanoparticles (GNPs) probes and said amine-containing chemical loaded liposomes, wherein said gold nanoparticles (GNPs) probes bind to said target analyte through an antibody, and wherein the amine-containing chemical is branched polyethylenimine, or a salt or derivative thereof;
    c) loading said liquid sample solution to the sample pad of the lateral flow strip and let the liquid sample migrate along the lateral flow strip to let the target analyte bind with the pre-loaded antibody on the capture area; and
    d) providing a detecting agent comprising gold nanoparticles and a hydrolytic agent and allowing the detecting agent to contact the lateral flow strip one or more times to generate a colorimetric signal that shows the existence of the target analyte, wherein the hydrolytic agent is capable of hydrolysis of said liposomes to release said amine-containing chemical.

2. The method of claim 1, wherein the target analyte comprises a pathogen.

3. The method of claim 2, wherein the pathogen is *Escherichia coli* O157:H7, *Salmonella* sp., *Listeria* sp., or any combination thereof.

4. The method of claim 1, wherein the amine-containing chemical is branched polyethylenimine, cysteine, salt or derivative therefore, or any combination thereof.

5. The method of claim 1, wherein the target analyte can be observed by naked human eyes through colored line and/or spot corresponding to the availability of the target analyte.

6. The method of claim 1, wherein the target analyte can be identified within one hour period.

7. The method of claim 1, wherein the method has no enzyme being used.

8. The method of claim 1, wherein the hydrolytic agent comprises polyoxyethylene (20) sorbitan monolaurate.

\* \* \* \* \*